(12) United States Patent
Ho et al.

(10) Patent No.: US 8,628,960 B2
(45) Date of Patent: Jan. 14, 2014

(54) DESICCATED BIOLOGICS AND METHODS OF PREPARING THE SAME

(75) Inventors: David H. Ho, McLean, VA (US); Stephen P. Bruttig, Murdock, NE (US)

(73) Assignee: Hememics Biotechnologies, Inc., Rockville, MD (US)

( * ) Notice: Subject to any disclaimer, the term of this patent is extended or adjusted under 35 U.S.C. 154(b) by 266 days.

(21) Appl. No.: 12/985,399

(22) Filed: Jan. 6, 2011

(65) Prior Publication Data
US 2011/0097795 A1   Apr. 28, 2011

Related U.S. Application Data

(60) Continuation of application No. 12/793,787, filed on Jun. 4, 2010, now abandoned, which is a division of application No. 12/234,824, filed on Sep. 22, 2008, now abandoned.

(60) Provisional application No. 60/974,806, filed on Sep. 24, 2007.

(51) Int. Cl.
*C12N 5/00* (2006.01)
*C12N 5/02* (2006.01)
*A01N 1/00* (2006.01)
*A01N 1/02* (2006.01)

(52) U.S. Cl.
USPC .................................. 435/374; 435/1.1; 435/2

(58) Field of Classification Search
USPC ............................................... 435/374, 1.1, 2
See application file for complete search history.

(56) References Cited

U.S. PATENT DOCUMENTS

| | | | |
|---|---|---|---|
| 2,353,985 A | 7/1944 | Barr | |
| 2,575,426 A | 11/1951 | Parnell | |
| 5,145,770 A * | 9/1992 | Tubo et al. | 435/1.3 |
| 5,378,601 A | 1/1995 | Gepner-Puszkin | |
| 5,629,145 A | 5/1997 | Meryman | |
| 5,648,222 A | 7/1997 | Tse et al. | |
| 5,780,295 A * | 7/1998 | Livesey et al. | 435/307.1 |
| 5,827,741 A | 10/1998 | Beattie et al. | |
| 6,127,177 A * | 10/2000 | Toner et al. | 435/374 |
| 6,221,575 B1 | 4/2001 | Roser et al. | |
| 6,268,012 B1 | 7/2001 | Sikora et al. | |
| 6,358,678 B1 | 3/2002 | Bakaltcheva et al. | |
| 6,436,705 B1 | 8/2002 | Bakaltcheva et al. | |
| 6,528,309 B2 | 3/2003 | Levine | |
| 6,723,497 B2 | 4/2004 | Wolkers et al. | |
| 6,743,575 B2 | 6/2004 | Wiggins et al. | |
| 6,770,478 B2 | 8/2004 | Crowe | |
| 6,841,168 B1 | 1/2005 | Worralli | |
| 6,913,932 B2 | 7/2005 | Maples et al. | |
| 6,919,172 B2 | 7/2005 | DePablo et al. | |
| 7,094,601 B2 | 8/2006 | Toner et al. | |
| 7,129,035 B2 | 10/2006 | Goldstein et al. | |
| 7,135,180 B2 | 11/2006 | Truong-Le | |
| 7,150,991 B2 | 12/2006 | Potts et al. | |
| 2001/0055583 A1 | 12/2001 | Roser et al. | |
| 2003/0017444 A1 | 1/2003 | Levine | |
| 2003/0175239 A1 | 9/2003 | Margolin et al. | |
| 2004/0110267 A1 | 6/2004 | Sundar | |
| 2004/0248293 A1 | 12/2004 | Toner et al. | |
| 2005/0277107 A1 | 12/2005 | Toner et al. | |
| 2006/0223050 A1 | 10/2006 | Crowe et al. | |
| 2007/0042339 A1 | 2/2007 | Toner et al. | |

FOREIGN PATENT DOCUMENTS

| | | |
|---|---|---|
| WO | 2002/046368 | 6/2002 |
| WO | 2007/078816 | 7/2007 |

OTHER PUBLICATIONS

Allison, S. D., et al., Optimization of storage stability of lyophilized actin using combinations of disaccharides and dextran, J. Pharm Sci. Feb. 2000;89(2):199-214.

Elversson, J., et al., Aqueous two-phase systems as a formulation concept for spray-dried protein, Int J Pharm. Apr. 27, 2005;294(1-2):73-87.

Pellerin-Mendes, C., et al., In vitro study of the protective effect of trehalose and dextran during freezing of human red blood cells in liquid nitrogen, Cryobiology. Sep. 1997;35(2):173-86.

Puhlev, I., et al., Desiccation tolerance in human cells, Cryobiology. May 2001;42(3):207-17.

Chen, T., et al, Beneficial effect of intracellular trehalose on the membrane integrity of dried mammalian cells, Cryobiology. Sep. 2001;43(2):168-81.

Moore et al., "The effects of Hypertonic Saline (7.5%) Dextran-70 (HSD) on human red cell typing, lysis and metabolism in Vitro," Letterman Army Institute of Research (1989) p. 1.

Reddy, T.S., et al, "Endothelial cell damage in human and rabbit corneas stored in K-Sol without antioxidants," Br. J. Opthalmol., Oct. 1989;73(10):803-808.

Huang, Z., et al., "Response of human cells to desiccation: comparison with hyperosmotic stress response," J. Physiol., 2004, 558(Pt. 1):181-191.

Chakrabortee, S., et al., "Hydrophilic protein associated with desiccation tolerance exhibits broad protein stabilization function," Biological Sciences/Cell Biology, PNAS, Nov. 2, 2007;104(46):18073-18078.

Lindemann, C.B., et al., "An investigation of the effectiveness of certain antioxidants in preserving the m motility of reactivated bull sperm models," Biology of Reproduction, 1988, 38:114-120.

Office Action dated Jun. 16, 2011 received in related U.S. Appl. No. 12/234,824.

(Continued)

*Primary Examiner* — Thaian N Ton
(74) *Attorney, Agent, or Firm* — Pepper Hamilton LLP

(57) ABSTRACT

The present invention provides compositions comprising desiccated biologics comprising a cell, protein, virus, nucleic acid, carbohydrate, or lipid, or any combination thereof, along with at least one membrane penetrable sugar, and at least one membrane impenetrable sugar, wherein the moisture content is from 5% to 95%, and to methods of preparing the same, and to methods of treating animals using the same.

16 Claims, 5 Drawing Sheets

(56) References Cited

OTHER PUBLICATIONS

Final Office Action dated Dec. 15, 2010 received in related U.S. Appl. No. 12/234,824.

Office Action dated Jul. 30, 2010 received in related U.S. Appl. No. 12/234,824.

Office Action dated Jul. 7, 2011 received in related U.S. Appl. No. 12/793,787.

* cited by examiner

DESICCATED BIOLOGICS AND METHODS OF PREPARING THE SAME

CROSS-REFERENCE TO RELATED APPLICATIONS

This application is a continuation of U.S. Ser. No. 12/793,787 filed Jun. 4, 2010, which is a divisional of U.S. Ser. No. 12/234,824 filed Sep. 22, 2008, which claims priority to U.S. provisional application Ser. No. 60/974,806 filed Sep. 24, 2007, each of which is incorporated herein by reference in its entirety.

FIELD OF THE INVENTION

The present invention is directed, in part, to compositions comprising desiccated biologics and to methods of preparing the same.

BACKGROUND OF THE INVENTION

Traditional preservation and storage of biologics, such as cells and biomolecules, usually involves special storage media, refrigeration, liquid nitrogen storage, or a highly specialized buffer solution. These biologics are usually used in a short period of time after their preparation to prevent spoilage due to the natural process of degradation and risks of pathogen contamination. For example, enucleated cells, such as platelets, have a shelf life at room temperature of only about 5 to 7 days. In addition, nucleated cells such as reproductive cells (Dinnyes et al., Reprod. Fertil. Dev., 2007, 19, 719-31), stem cells (De Sousa et al., Reproduction, 2006, 132, 681-9) and hepatocytes (Bakala et al., Pol. J. Vet. Sci., 2007, 10, 11-8) must be maintained in expensive storage devices and possess limited shelf-life at room temperature.

There have been several attempts to extend the shelf life of cells. Some of these methods are reported in, for example, U.S. Pat. Nos. 7,150,991; 7,135,180; 7,094,601; 6,841,168; 6,723,497; 6,770,478; 5,827,741; and 5,629,145; and in the following literature: Palev et al., Cryobiology, 2001, 42, 207-17; Ma et al., Cryobiology, 2005, 51, 15-28; Matsuo, Br. J. Ophthalmol., 2001, 85, 610-2; McGinnis et al., Biol. Reprod., 2005, 73, 627-33; Gordon et al., Cryobiology, 2001, 43, 182-7; Bhowmick et al., Biol. Reprod., 2003, 68, 1779-86; Meyers, Reprod. Fertil. Dev., 2006, 18, 1-5; Chen et al., Cryobiology, 2001, 43, 168-81; Wolkers et al., Cryobiology, 2001, 42, 79-87; Crowe et al., Arch. Biochem. Biophys., 1983, 220, 477-84; Chen et al., Cryobiology, 1993, 30, 423-31; and U.S. Pat. No. 6,528,309.

Current technologies of cell preservation often focus on freeze-drying as a means for preserving cells in the dry state. Freezing cells, however, can promote ice crystal formation as well as osmotic changes during the process and result in disruption of intracellular organelles and membranes, resulting in loss of cells (i.e., transient warming effect) or loss or significant diminution of cell functions. Further, freeze-drying can, and often does, result in generating microparticles that are apparently formed from the cellular debris. As pointed out from a report involving various freezing protocols for hepatocyte suspensions, mostly devastating results such as low recovery and severe loss of functions occurred (Koebe et al., Chem. Biol. Interact., 1999, 121, 99-115). In another report, experiments showed that a mechanical interaction between ice crystals and red blood cell membrane induced mechanical damage to the membrane (Ishiguro et al., Cryobiology, 1994, 31, 483-500).

Thus, in many instances, the current protocols for preserving and/or storing biologics, whether via lyophilization, freeze-drying, vacuum dry and/or oven dry methods, are not sufficient to dry cells and to recover desired functions upon reconstitution. As can be immediately recognized, there is a need in the art for preservation and/or storage alternatives to extend shelf life of biologics for therapy, diagnostics and research. Accordingly, the present invention provides methods of preserving and/or storing biologics to preserve cell structures and functions in the dried or semi-dried states. These processes can result in cells that will recover full or partial function upon reconstitution and rehydration.

SUMMARY OF THE INVENTION

The present invention provides compositions comprising: one or more biologics; one or more membrane penetrable sugars; and one or more membrane impenetrable sugars; wherein the moisture content of the composition is from about 5% to about 95%.

In some embodiments, the biologic is a cell. In some embodiments, the cell is anucleated. In some embodiments, the anucleated cell is a platelet or red blood cell. In some embodiments, the cell is nucleated. In some embodiments, the nucleated cell is a white blood cell, a stem cell, a stem cell progenitor cell, a gamete, a gamete progenitor cell, a hepatocyte, a muscle cell, an endothelial cell, an epithelial cell, an erythroblast, a leukoblast, a chondroblast, or a pancreatic cell or other nucleated cell. In some embodiments, the biologic is a virus, protein, nucleic acid, carbohydrate, or lipid.

In some embodiments, the membrane penetrable sugar is trehalose. In some embodiments, the membrane impenetrable sugar is dextran. In some embodiments, the membrane impenetrable sugar is a combination of more than one sugar (e.g., a mixture of dextran and other sugars with a molecular weight of 50,000 Daltons or more).

In some embodiments, the moisture content is from about 15% to about 40%. In some embodiments, the moisture content is from about 20% to about 25%. In some embodiments, the moisture content is from about 55% to about 60%. In some embodiments, the moisture content is from about 60% to about 95%.

In some embodiments, the biologic is a platelet, the membrane penetrable sugar is trehalose, the membrane impenetrable sugar is dextran, and the moisture content is about 15%. In some embodiments, the biologic is a red blood cell, the membrane penetrable sugar is trehalose, the membrane impenetrable sugar is dextran, and the moisture content is about 25%. In some embodiments, the biologic is a white blood cell, the membrane penetrable sugar is trehalose, the membrane impenetrable sugar is dextran, and the moisture content is about 50%. Thus, dependent on the type of cells, the membrane penetrable sugar is trehalose, the membrane impenetrable sugar is dextran alone or in combination with another sugar(s) with a molecular weight of 50,000 Daltons or more, and the moisture content is from about 15% to about 90%.

The present invention also provides methods of preserving a biologic comprising: contacting the biologic with at least one membrane penetrable sugar and at least one membrane impenetrable sugar; optionally, contacting the biologic with a fixative agent; and drying the biologic by vacuum desiccation to a final moisture content of from about 5% to about 95%.

In some embodiments, the biologic is a cell. In some embodiments, the cell is anucleated. In some embodiments, the anucleated cell is a platelet or red blood cell. In some embodiments, the cell is nucleated. In some embodiments, the nucleated cell is a white blood cell, a stem cell, a stem cell progenitor cell, a gamete, a gamete progenitor cell, a hepatocyte, a muscle cell, an endothelial cell, an epithelial cell, an erythroblast, a leukoblast, a chondroblast, or a pancreatic cell, or other nucleated cell. In some embodiments, the biologic is a virus, protein, nucleic acid, carbohydrate, or lipid.

In some embodiments, the membrane penetrable sugar is trehalose. In some embodiments, the membrane impenetrable sugar is dextran.

In some embodiments, the moisture content is from about 15% to about 40%. In some embodiments, the moisture content is from about 20% to about 25%.

In some embodiments, the fixative agent is glutaraldehyde or paraldehyde.

In some embodiments, the biologic is dried by vacuum desiccation from about 0° C. to about 40° C. for about 1 hours to about 24 hours. In some embodiments, the biologic is dried by vacuum desiccation from about 32° C. to about 34° C. for about 3 hours.

In some embodiments, the method further comprises storing the biologic in a vacuum sealed container in the presence or absence of a desiccant. In some embodiments, the method further comprises rehydrating the biologic. In some embodiments, the rehydration comprises contacting the biologic with water, followed by saline.

In some embodiments, the biologic is a platelet, the membrane penetrable sugar is trehalose, the membrane impenetrable sugar is dextran, and the moisture content is about 15%. In some embodiments, the biologic is a red blood cell, the membrane penetrable sugar is trehalose, the membrane impenetrable sugar is dextran, and the moisture content is about 25%. In some embodiments, the biologic is a white blood cell, the membrane penetrable sugar is trehalose, the membrane impenetrable sugar is dextran, and the moisture content is about 50%.

DESCRIPTION OF EMBODIMENTS

Figure 1:
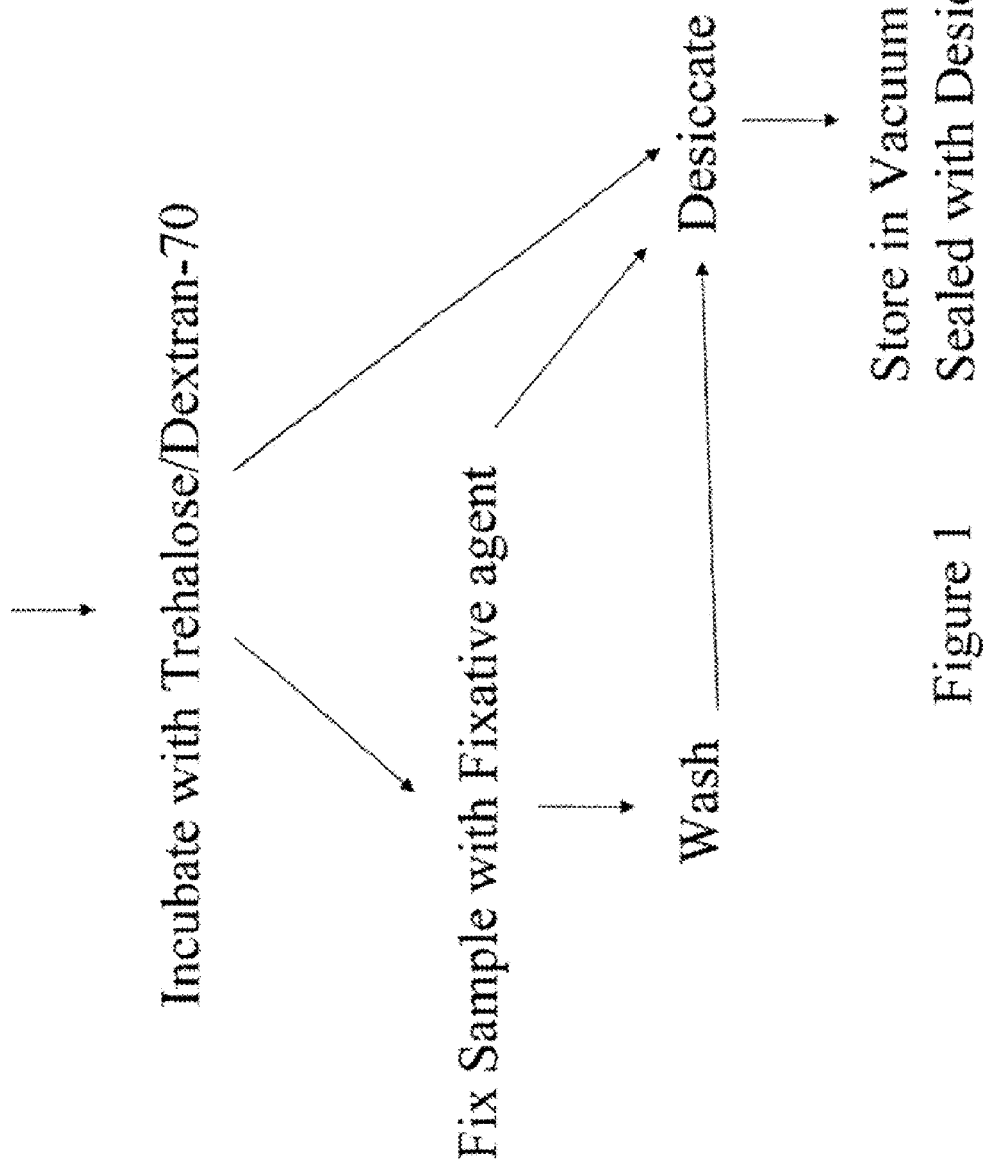
FIG. 1 shows a schematic representation of a representative desiccation process.

The present invention provides methods of preserving and/or storing biologics, individually, together, or in combination in a dried or semi-dried format. The present invention also provides compositions comprising a biologic in a desiccated state.

As used herein; the term "biologic" means a cell and/or a biomolecule.

As used herein, the term "cell" means nucleated cells (i.e, cells containing one or more nuclei) or anucleated cells (i.e., platelets and red blood cells; cells that have no nucleus). Cells may be in the form of individual cells, tissue(s), and/or organ(s). Cells can be derived from any organ. Different cells can be present in the same sample being desiccated. In addition, cells can be altered by humans such as, for example, cell lines and hybridomas. Cells include animal cells and/or plant cells.

As used herein, the term "biomolecule" means any protein, nucleic acid, carbohydrate, lipid, or other such molecule, produced or existing free in other body/biological fluids. Biomolecules can be present alone, or in combination with other biomolecules and/or cells, such as plasma products (i.e., blood cells, biomolecules, and salts), tissue, and/or organs, such as the vasculature bed containing endothelial cells, smooth muscle cells and some combination of other cell types. Biomolecules also include, for example, antibodies and peptides, or compositions of biomolecules such as, for example, the proteins, peptides, and other biological organic molecules in plasma.

The present invention provides compositions comprising: one or more biologics; one or more membrane penetrable sugars; and one or more membrane impenetrable sugars; wherein the moisture content of the composition is from about 5% to about 95%.

In some embodiments, the biologic is a cell. In some embodiments, the cell is anucleated. Examples of anucleated cells include, but are not limited to, a platelet and a red blood cell. In some embodiments, the anucleated cell is present at from about $1 \times 10^3$ cells/mL to about $1 \times 10^{10}$ cells/mL. In some embodiments, the anucleated cell is present at about $1 \times 10^9$ cells/mL.

In some embodiments, the cell is nucleated. Examples of nucleated cells include, but are not limited to, a white blood cell (i.e., a T cell, a B cell, a macrophage, a neutrophil, a lymphocyte, and the like), a stem cell (i.e, adult and/or neonatal, various tissues or species origin), a stem cell progenitor cell, a gamete (male and/or female), a gamete progenitor cell, and a cell derived from an organ including, but not limited to, various hepatocytes, various kidney cells, various neural cells, various cardiac cells, a muscle cell, an endothelial cell, an epithelial cell, various skin cells, chondrocytes, an erythroblast, a leukoblast, a chondroblast, a pancreatic cell, and the like. In some embodiments, the cell is a cell line such as, for example, Chinese hamster ovary (CHO) cells, 3T3 fibroblasts, HEK cells, and the like. In some embodiments, the nucleated cell is an islet cell or cord blood cell. In some embodiments, the nucleated cell is a human venous, arterial, or capillary endothelial cell, or the like. The cells used herein can be obtained from or derived from animals including, but not limited to, reptiles, amphibians, birds, fish, mammals, and the like. Mammals include, but are not limited to, humans, dogs, cats, horses, pigs, cows, rabbits, goats, and the like. The compositions described herein can be used, for example, in both human medical and veterinary medical applications, as well as in research endeavors. In some embodiments, the nucleated cell is present at from about $1 \times 10^3$ cells/mL to about $1 \times 10^{10}$ cells/mL. In some embodiments, the anucleated cell is present at about $1 \times 10^7$ cells/mL.

In some embodiments, the biologic is a virus, protein, nucleic acid, carbohydrate, or lipid, or a combination thereof. In some embodiments, the biologic is an antibody or peptide. In some embodiments, the biologic is an antibiotic, a hormone, an enzyme, a clotting factor, or the like. In some embodiments, the biologic is present at from about 0.001 mg/mL to about 50 mg/mL. In some embodiments, the biologic is present at about 5 mg/mL.

In some embodiments, the membrane penetrable sugar is chosen from trehalose, glucose, sucrose, lactose, maltose, other mycoses, and the like, to protect membrane-bound as well as free cytosolic enzyme systems and other critical cellular metabolic systems and pathways. Additionally, such treatments help ensure that upon water removal, the changes in cell volume and shape, condensation and crowding of the cytoplasm, membrane phase transitions, loss of supercoiling of DNA, oxidative damage, and metabolic arrest can be minimized. In some embodiments, the membrane penetrable sugar is trehalose. The membrane penetrable sugar is generally a non-reducing sugar. Such a sugar may act to stabilize the cell for the drying processes described herein. In some embodiments, the membrane penetrable sugar can be replaced with other saccharides, proteins, polymers, and agents that function in the same manner. In some embodiments, the membrane penetrable sugar is present at from about 0.1% w/v to about 12% w/v. In some embodiments, the membrane penetrable sugar is present at about 3% w/v. In some embodiments, the trehalose is not introduced within a cell by a viral vector. In some embodiments, the cells are not thermally shocked to allow trehalose to enter the cells. In some embodiments, the cells are not osmotically shocked to allow trehalose to enter the cells. In some embodiments, trehalose is not combined with glycerol or mannitol.

In some embodiments, the membrane impenetrable sugar is chosen from dextran, starches, amylase, amylopectin, glycogen, polysucrose, and the like. In some embodiments, the membrane impenetrable sugar is dextran. In general, sugars with molecular weight greater than or equal to 50,000 daltons, such as polysaccharides having a general formula of $C_n(H_2O)_{n-1}$ where n is from about 200 to about 2500, or $(C_6H_{10}O_5)_n$ where n is front about 40 to about 3000, can be used. Additionally, mix-type sugars such as, for example, Xanthan gum, guar gum, starch gum, British gum, and the like can be used as membrane impenetrable sugars. The membrane impenetrable sugar is generally neutral. In some embodiments, the membrane impenetrable sugar can be replaced with other saccharides, proteins, polymers, and agents that function in the same manner. In some embodiments, the membrane impenetrable sugar can be replaced with plasma proteins such as, for example, albumin, soluble starches, glycogen, soluble chitin, and soluble celluloses. In some embodiments, the membrane impenetrable sugar is present at from about 0.01% w/v to about 25% w/v. In some embodiments, the membrane impenetrable sugar is present at about 3% w/v.

In some embodiments, the cells or biomolecules are treated with at least one membrane impenetrable sugar and at least one membrane penetrable sugar in the absence of any polyol (i.e., a polyhydric alcohol, such as glycerol).

To protect the extracellular milieu under the dried or semi-dried conditions, it is proposed that the membrane impenetrable sugars be used to ensure that cells can be viable in a depleted state, metabolically adaptive, and maintenance in favorable local hydration conditions. Other protective agents include, for example, proteins or the like, and hydrocolloid or the like. Such treatments/processes are intended to stabilize both internal and external membranes.

In some embodiments, the composition further comprises a "fluidizer" or the like, such as an extremely mild mixture of glycerol or the like with a minimal, but effective, amount of an omega-3 fatty acid, or the like (e.g., EPA, ALA, etc.). To maintain membrane flexibility, the use of glycerol, or the like should be limited, as the goal is not to "permeabilize" the cell, but rather, to deliver both the glycerol or the like and omega-3 fatty acid or the like into the cell for incorporation into the cell membrane. Additional fluidizers include, but are not limited to, dimethylsulfoxide (DMSO), glycerin, and various detergents such as Tween-80. In some embodiments, the fluidizer is present at from about 1 nM to about 200 mM. In some embodiments, the fluidizer is present at from about 10 µM to about 50 µM.

In some embodiments, the composition further comprises a fixative agent, such as a cross-linker with an aldehyde function such as, for example, paraformaldehyde, glutaraldehyde, or another compound having two terminal aldehyde groups. A fixative agent may provide cells with physical stability such as volume and shape, which may be helpful for the use of cells as control reagents sixe simulants and provide uniformity across multiple instrument technologies. In some embodiments, the fixative agent is present at from about 0.01% to about 10%. In some embodiments, the fixative agent is present at about 0.5%.

In some embodiments, the moisture content of the composition is from about 5% to about 95%. In some embodiments, the moisture content is from about 10% to about 90%. In some embodiments, the moisture content is from about 15% to about 85%. In some embodiments, the moisture content is from about 20% to about 80%. In some embodiments, the moisture content is from about 25% to about 75%. In some embodiments, the moisture content is from about 30% to about 70%. In some embodiments, the moisture content is from about 35% to about 65%. In some embodiments, the moisture content is from about 40% to about 60%. In some embodiments, the moisture content is from about 45% to about 55%. In some embodiments, the moisture content is from about 5% to about 30%. In some embodiments, the moisture content is from about 5% to about 25%. In some embodiments, the moisture content is from about 5% to about 20%. In some embodiments, the moisture content is from about 5% to about 30%. In some embodiments, the moisture content is from about 20% to about 25% or from about 15% to about 25%. In some embodiments, the moisture content is about 25%. In some embodiments, the moisture content is about 15%.

In some embodiments, platelets are dried to no less than 15% residual moisture. In some embodiments, red blood cells are dried to no less than 25% residual moisture. In some embodiments, B cells are dried to no less than about 50% to 90% residual moisture.

In some embodiments, the biologic is a platelet, the membrane penetrable sugar is trehalose, the membrane impenetrable sugar is dextran, and the moisture content is about 15%.

In some embodiments, the biologic is a red blood cell, the membrane penetrable sugar is trehalose, the membrane impenetrable sugar is dextran, and the moisture content is about 25%.

In some embodiments, the biologic is a white blood cell, the membrane penetrable sugar is trehalose, the membrane impenetrable sugar is dextran, and the moisture content is about 50%.

In some embodiments, the biologic is a protein, virus, or plasma, the membrane penetrable sugar is trehalose, the membrane impenetrable sugar is dextran, and the moisture content is from about 5% to about 10%.

The present invention also provides methods of preserving a biologic comprising: contacting the biologic with at least one membrane penetrable sugar and at least one membrane impenetrable sugar; optionally, contacting the biologic with a fixative agent; and drying the biologic by vacuum desiccation to a final moisture content of from about 5% to about 90% (see, FIG. 1).

The biologic being preserved can be any of the cells or biomolecules described herein. The membrane penetrable sugar can be any of the membrane penetrable sugars described herein. The membrane impenetrable sugar can be any of the membrane impenetrable sugars described herein. The fixative agent can be any of the fixative agents described herein. The moisture content can be any of the ranges or values of moisture content described herein.

In general, the methods comprise concentrating the cells or biomolecules, and suspending the cells or biomolecules in a dehydrating salt buffer that is comprised of the membrane penetrable sugar and the membrane impenetrable sugar. Additionally, the cells can be fixed with a fixative agent to provide physical stability prior to the drying process. The cell/biomolecule media compositions are then dried using a desiccator.

In some embodiments, cells are washed through the process of centrifugation and resuspension in an appropriate buffer. The membrane penetrable and membrane impenetrable sugars are added to the cells. In some embodiments, a low concentration of adenosine is added to increase cellular ATP via the purine-based ATP "salvage pathway." In some embodiments, superoxide dismutase (SOD) is added to effectively scavenge cellular oxygen free radicals. In some embodiments, a membrane fluidizer, such as an extremely mild mixture of glycerol or the like, together with a minimal but effective amount of omega-3 fatty acid or the like (e.g., EPA, ALA, etc.), is added. In some embodiments, adenosine is present at from about 1 nM to about 100 mM. In some embodiments, adenosine is present at about 70 μM. In some embodiments, SOD is present at from about 1 nM to about 5 mM. In some embodiments, SOD is present at from about 1 μM to about 3 μM.

In some embodiments, the cell is dried by vacuum desiccation at from about 0° C. to about 40° C. In some embodiments, the cell or other biologic is dried for about 1 hour to about 4 hours, or for about 1 hour to about 8 hours, or for about 1 hour to about 12 hours, or for about 1 hour to about 16 hours. In some embodiments, the cell is dried by vacuum desiccation at from about 32° C. to about 34° C. for about 3 hours. To mitigate the development of ice crystal formation, freezing and thawing of cells should be avoided. Water molecules should be removed at temperatures from about 0° C. to about 40° C., at about atmospheric pressure (i.e., about 760 mmHg) or at pressures reduced from atmospheric pressure (i.e., less than about 760 mmHg, or about 560 mmHg). The rate of water removal should be controlled depending on the cell type. The rate of water removal should not be too fast to cause the overall collapse of the cell structure but not too slow to promote cellular activities that could compromise the cellular integrity and metabolism and defeat the drying process. The final moisture level can be from about 5% to about 95% dependent on cell type and the final use.

The cells destined to undergo such treatment can be dried via a process of desiccation such as vacuum drying or convection oven drying. The cells can be transferred to a nitrogen-filled, mildly heated desiccator with less than 5% humidity and gradually dried over a period of time until the composition contains a moisture level consistent with the needs of the specific application. Other suitable gasses include, but are not limited to, essentially inert gasses such as helium, argon, or xenon. The gasses can be introduced into the chamber at or near the end of the process to drive off any remaining free oxygen. In some embodiments, the process begins at ambient humidity, which should be as low as reasonably achievable (e.g., about 50%). During desiccation, however, no artificial humidification is required and the vacuum desiccator keeps the chamber humidity very low (i.e., at about 5%). In some embodiments, there is an absence of oxygen in the desiccation chamber upon vacuum drying.

Figure 2:
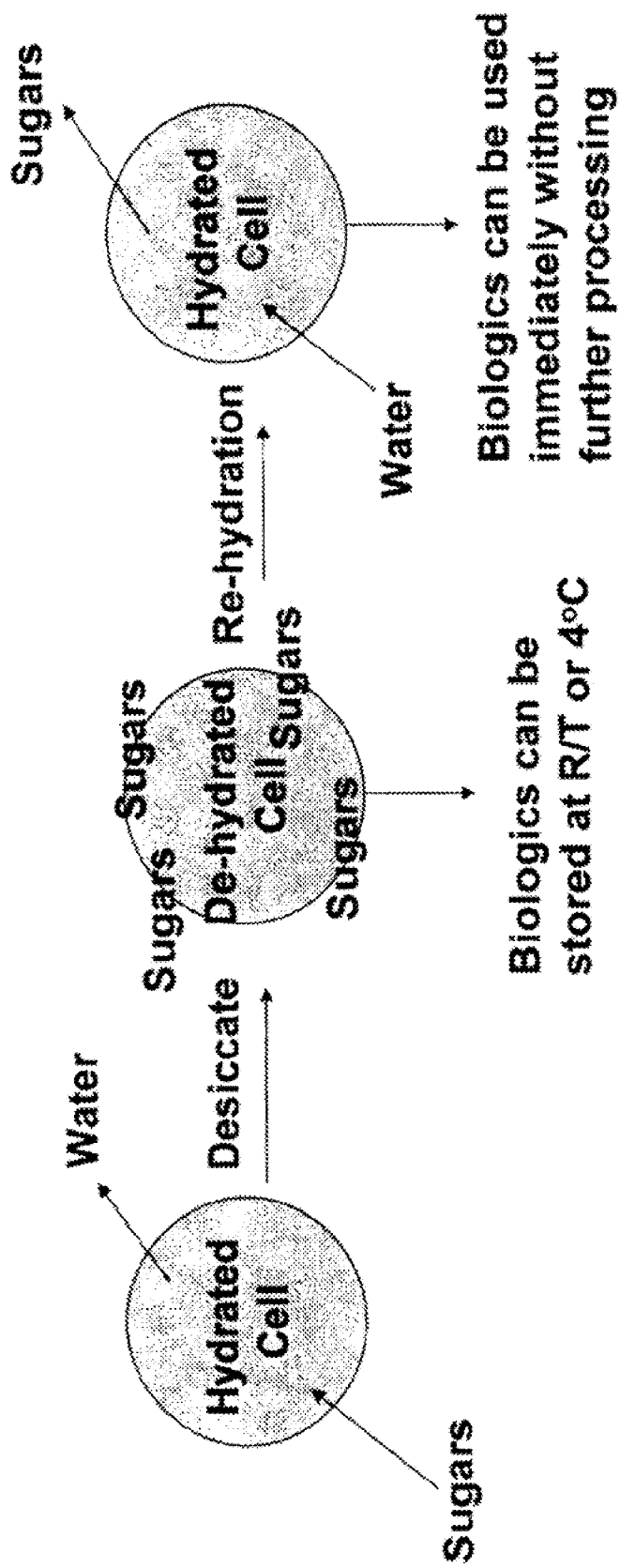
FIG. 2 shows a schematic representation of sugar uptake to stabilize the cells in dry format and a hydration process.

In some embodiments, the methods further comprise storing the cells in a vacuum sealed container in the presence or absence of a desiccant, and the presence or absence of nitrogen or other inert gas. Desiccants are well known to the skilled artisan and are commercially available and include, but are not limited to, silica gel, calcium sulfate, and calcium chloride. Desiccants can be included to mitigate humidity issues and absorb moisture and gases that may be released by the cells during the storage period. The desiccated cells can be stored under vacuum for long-term storage (see, FIG. 2). In some embodiments, the cells or biomolecules can be stored for at least 7 days prior to rehydration and subsequent use. In some embodiments, the cells or biomolecules can be stored for at least 10 days prior to rehydration and subsequent use. In some embodiments, the cells or biomolecules can be stored for at least 14 days prior to rehydration and subsequent use. In some embodiments, the cells or biomolecules can be stored for at least 21 days prior to rehydration and subsequent use. In some embodiments, the cells or biomolecules can be stored for at least 28 days prior to rehydration and subsequent use. In some embodiments, the cells or biomolecules can be stored for at least 45 days prior to rehydration and subsequent use. In some embodiments, platelets and/or red blood cells can be stored for greater that 45 days.

In some embodiments, the methods further comprise rehydrating the cells. In some embodiments, rehydration comprises contacting the cells with water and, optionally, next with saline. In some embodiments, the volume of the fluid added to the cells is equal to the fluid volume of the composition prior to the drying process. Cells and biomolecules can be rehydrated to the concentrations described above. Instead of water, or water and saline, various physiological buffers including, but not limited to, HEPES, phosphate buffered saline (PBS), Tris buffer, and the like, or other such solutions, can be used.

The time and temperature for carrying out the rehydration process can be from about 5 minutes to about 200 minutes at room temperature or temperature up to 37° C. The optimal reconstitution time and temperature will be dependent of cell type and the final use and can be determined by the user. In some embodiments, temperatures from about 22° C. to about 37° C. can be used for rehydration. Rehydration time can vary with the procedural factors, expected cell or protein performance, residual moisture, and volume of dried material. In some embodiments, the time for rehydration is from about 1 hour to about 24 hours prior to desired use.

In some embodiments, the viability of the rehydrated cells is about 10% or greater, about 20% or greater, about 25% or greater, about 30% or greater, about 40% or greater, about 50% or greater, about 60% or greater, about 70% or greater, about 75% or greater, about 80% or greater, about 85% or greater, about 90% or greater, about 95% or greater, or about 99% or greater.

In some embodiments, the methods comprise preserving a platelet comprising: contacting the platelet with at least one membrane penetrable sugar that is trehalose and at least one membrane impenetrable sugar that is dextran; optionally, contacting the platelet with a fixative agent that is glutaraldehyde or paraldehyde; and drying the platelet by vacuum desiccation to a final moisture content of about 15%.

In some embodiments, the methods comprise preserving a red blood cell comprising: contacting the red blood cell with at least one membrane penetrable sugar that is trehalose and at least one membrane impenetrable sugar that is dextran; optionally, contacting the red blood cell with a fixative agent that is glutaraldehyde or paraldehyde; and drying the red blood cell by vacuum desiccation to a final moisture content of about 25%.

In some embodiments, the methods comprise preserving a white blood cell comprising: contacting the white blood cell with at least one membrane penetrable sugar that is trehalose and at least one membrane impenetrable sugar that is dextran; optionally, contacting the white blood cell with a fixative agent that is glutaraldehyde or paraldehyde; and drying the white blood cell by vacuum desiccation to a final moisture content of about 50%.

In some embodiments, the methods comprise preserving a protein, virus, or plasma comprising: contacting the protein, virus, or plasma with at least one membrane penetrable sugar that is trehalose and at least one membrane impenetrable sugar that is dextran; optionally, contacting the protein, virus, or plasma with a fixative agent that is glutaraldehyde or paraldehyde; and drying the protein, virus, or plasma by vacuum desiccation to a final moisture content of from about 5% to about 10%.

The present invention also comprises methods of treating an animal having a need for a biologic comprising administering a biologic described herein. In some embodiments, the animal will be a human suffering from a blood disorder whereby the human is in need of a blood product (i.e., whole blood, red blood cells, platelets, plasma, clotting factor(s), etc). The need may arise from the human having a disease, condition, or disorder whereby the particular biologic is not produced or is produced in insufficient amounts. Alternately, the need may arise from injury, such as a traumatic injury characterized by blood loss. Any of the rehydrated vacuum dried biologics described herein can be administered to such animals. The need can be for any biologic for correlated with appropriate diseases, conditions, or disorders. Exemplary diseases, conditions, or disorders include, but are not limited to, anemia, blood loss, and hemophelia.

The present invention also provides any of the compositions described herein for treating an animal in need of a biologic, as described above. The present invention also provides any of the compositions comprising a biologic described herein for use in the manufacture of a medicament, such as a sterile medicament, for the treatment of a disease, condition, or disorder related to the particular biologic. In one example, the medicament is a sterile composition comprising whole blood, red blood cells, platelets, plasma, clotting factor (s), etc. for the treatment of someone in need thereof.

In some embodiments, the vacuum desiccated cells that have been rehydrated show surface marker profiles, such as platelet surface marker, similar to fresh cells.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to known methods using commercially available reagents, except where otherwise noted.

EXAMPLES

Example 1

Desiccation of Red Blood Cells (RBC) (Actual Example)

The process of isolating and washing red blood cells from whole blood is well known in the art. Thus, numerous methods can be used to generate washed red blood cells and prepare them for the desiccation processes described herein. The following is meant to serve as one example of how the process is typically performed.

Blood was obtained in a sterile manner using an anti-coagulating agent such as sodium citrate, heparin, ethylenediaminetetraacetic acid (EDTA), or the like. A 10 mL aliquot of whole blood was placed into a 15 mL conical tube and then centrifuged at 100 g for 30 minutes to remove the platelet rich plasma.

To wash RBC, the overall packed RBC volume was determined, and a minimum of three times that volume of saline (0.9% NaCl) was added. For example, if the packed RBC volume is 1 mL, a minimum of 3 mL of saline was added. The cells were suspended by inverting the tube several times. Another centrifugation at 100 g for 30 minutes was performed. The saline supernatant was removed and discarded, and the wash process was repeated again.

To get RBCS ready for desiccation, a concentrated dehydration buffer (cDHB) was prepared fresh. To make cDHB, a saline solution (0.9% NaCl) containing 100 mM HEPES was used, to which was added 200 µM adenosine, 100 mM glucose, 10 mM $K_2HPO_4$, 10% Dextran-70, and 12% trehalose. The overall packed RBC volume was determined, and multiplied by 4 to obtain the final desired volume. The final volume was obtained by adding in ¾th the volume with saline and ¼th the volume with cDHB. The final ¼th volume was the cell pellet. For example, if the packed RBC volume was 1 mL, then the final volume should be 4 mL. To obtain this volume, 2 mL of saline and 1 mL of cDHB were added. The cells were resuspended by inverting the tubes several times. The RBC were incubated in the buffer for 1 hour at 32° C.-37° C. or alternately, in 4° C. for 24 hours or up to 48 hours.

For desiccation of RBC, the weight of the empty container (tare weight) was determined. In general, a vial, made from any materials that are non-reactive to cells and proteins, can be used for this purpose. To desiccate 1 mL of an RBC solution, a tall vial with 10 mL capacity can be used. This is to account for the "wicking" of the solution up the walls of the vial in a vacuum environment. For example, a 1 mL aliquot of RBC solution was placed into the vial, which was then weighed again (pre-dehydration weight). The temperature of the dehydration chamber was adjusted to 32° C.-37° C. and the aliquot of RBC solution was dehydrated with vacuum at −560 mmHg open system for 90 or more minutes. The final moisture content was about 15%.

The following formula describes the calculation of % moisture:

$$\% \text{ Moisture} = \left[\frac{(\text{Weight of vial after dehydration} - \text{Weight of empty vial})}{(\text{Weight of vial before dehydration} - \text{Weight of empty vial})}\right] \times 100\%$$

Example 2

Desiccation of Red Blood Cells (RBC) with Fixative Agent (Actual Example)

RBC were processed and prepared as outlined in Example 1. After determining the overall packed RBC volume and multiplying this volume by 4 to obtain the final volume (as described above in Example 1), the final volume was obtained by adding in ⅔th the volume with saline and ¼th the volume with fixative buffer. For example, if the packed RBC volume was 1 mL, then the final volume should be 4 mL. To obtain this volume, 2 mL of saline and 1 mL of fixative buffer was added. The cells were suspended by inverting the tubes several times. The RBCS were incubated in the fixative buffer for as little as one hour at 34° C. or as lung as 24 hours at 4° C.

To prepare the fixative buffer with fixative agent, the fixative agent was added to the cDHB such that the final concentration of the fixative agent was 0.5%. The fixative buffer was kept in the cold at 4° C. for at least 30 minutes before use.

For desiccation of RBC with a fixative agent, the cells were centrifuged at 100 g for 30 minutes to remove the fixative buffer. The overall packed RBC volume was determined and multiplied by 4 to obtain the final volume. The final volume was obtained by adding in ⅔th the volume with saline and ¼th the volume with cDHB. For example, if the packed RBC volume was 1 mL, then the final volume should be 4 mL. To obtain this, 2 mL of saline and 1 mL of cDHB were added. The cells were suspended by inverting the tubes several times.

The RBCs were desiccated as described above in Example 1.

Vials were sealed under vacuum and/or under nitrogen gas. Samples were packed under vacuum with appropriate gas as well as having a desiccant to control and absorb moisture or gas that may be released by cells under storage. The dried RBC vials were kept at 4° C. or at room temperature.

Figure 3:
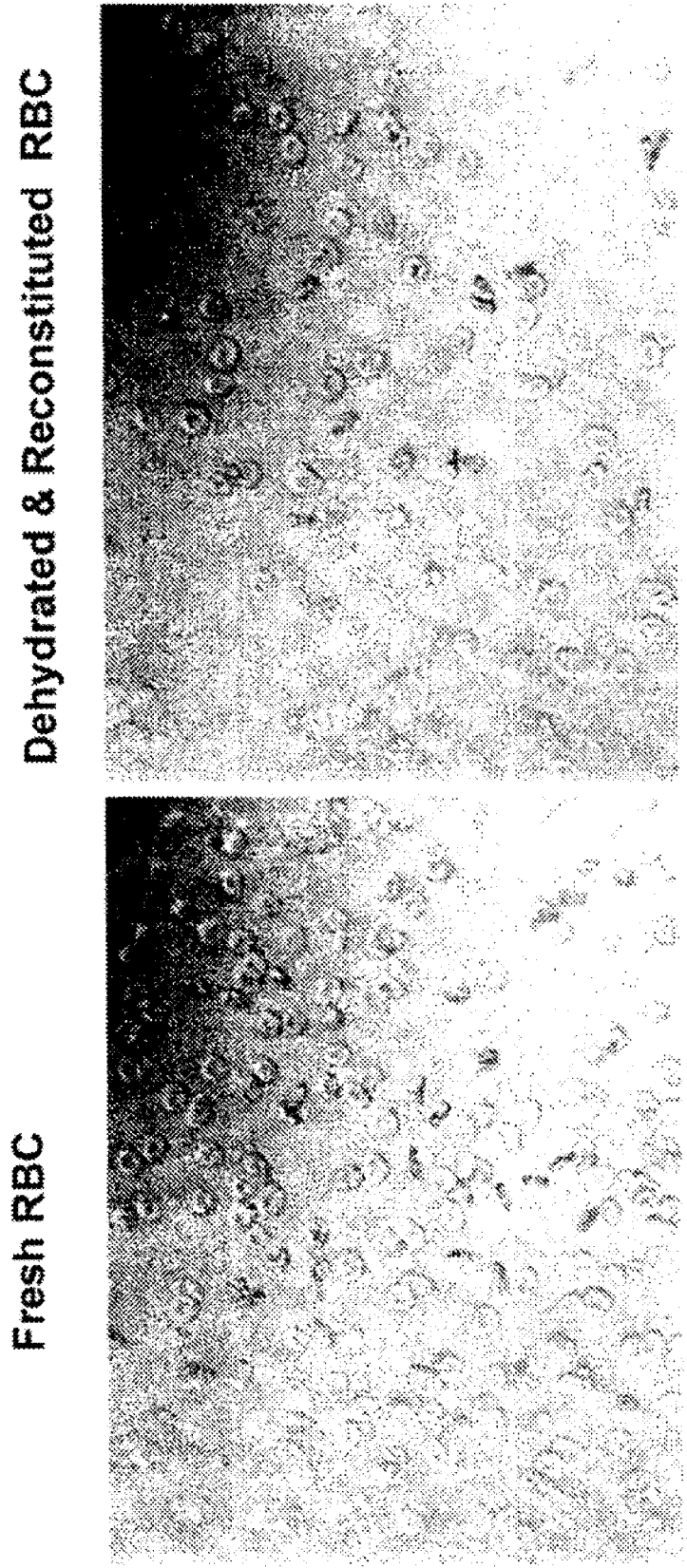
FIG. 3 shows hydration of desiccated red blood cells compared to fresh blood cells where the cells in both panel maintain the bi-concave structures.

Depending on the final moisture content, but in general, 0.75 mL of water was used for reconstitution. The recommended volume of distilled water was gently pipetted onto the wall of the vial and was allowed to contact the dried cells via gravity. The time and temperature for reconstitution ranged from 5 minutes to 200 minutes at room temperature or a temperature up to 37° C. The desired reconstitution time and temperature will be dependent on the cell type and the final use. In general, the reconstituted vial was left on a flat surface for 2 hours with gentle swirling every 15 minutes to rehydrate the cells. FIG. 3 depicts typical structure appearance of fresh red blood cells and the same cells, which were reconstituted after being desiccated. The reconstituted cells maintained the familiar bi-concave structures, which is the hallmark of functional red blood cells.

Example 3

Desiccation of Platelet Rich Plasma (PRP) (Actual Example)

The process of isolation of PRP from whole blood is well known in the art. Thus, numerous methods can be used to generate PRP and prepare them for the desiccation process. The following is meant to serve as one example of how the process is typically performed.

Blood was obtained in sterile manner using an anti-coagulating agent such as sodium citrate, heparin, EDTA, or the like. A 10 mL aliquot of whole blood was placed into a 15 mL conical tube. The whole blood was centrifuged at 100 g for 30 minutes to separate PRP from white blood cells and red blood cells. The PRP was decanted from the centrifuge tube containing blood cells to a new tube with no red or white blood cells. cDHB was prepared as described in Example 1. The overall PRP volume was determined, and ¼th of the cell volume, as cDHB, was added. For example, if the PRP volume is 4 mL, 1 mL of cDHB was added and then mixed by inverting the tubes several times. The PRP solution was incubated at 34° C. for 1 hour with mixing every 10 minutes.

For desiccation of PRP, the weight of the empty container (tare weight) was determined. Again, a vial made from any materials that are non-reactive to cells and proteins, was used for this purpose. To desiccate 1 mL of PRP solution, a vial with a 10 mL capacity was used. For example, a 1 mL aliquot of PRP solution was placed into the vial, which was then weighed (pre-dehydration weight). The temperature of the dehydration chamber was adjusted to 32° C.-37° C. and dehydrated under vacuum at −560 mmHg open system for 90 minutes or more. The final moisture content was about 15%. The formula in Example 1 was used to calculate the final % moisture.

Figure 4:
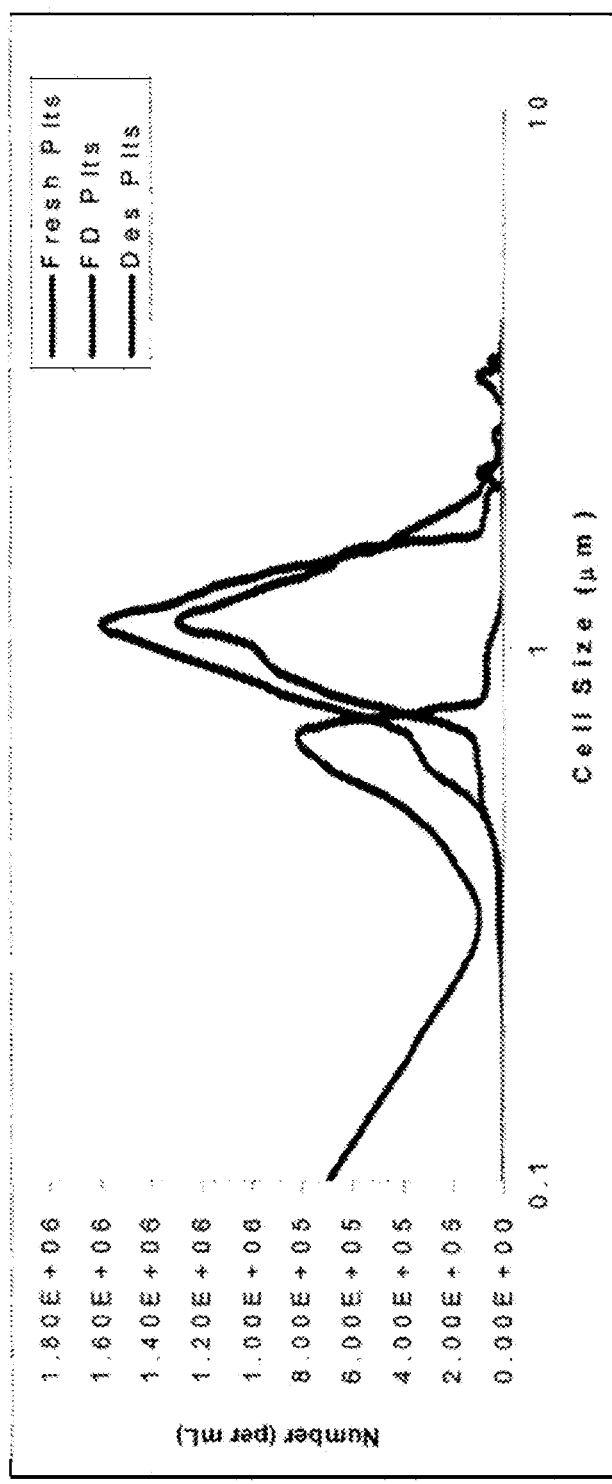
FIG. 4 shows platelet-sizing profile using Freeze-drying (FD Plts) and Desiccation (Des Pits) technique compared to fresh platelets.

FIG. 4 depicts typical size distribution of fresh PRP (labeled as fresh platelets) and the same cells which were reconstituted after being desiccated (Des Platelets) or freeze-dried (FD Platelets). As can be seen, the size distribution of the desiccated platelets using the current process was similar to that of fresh platelets, whereas the size distribution of the freeze-dried platelets included platelets that were fragmented and those that were much smaller when compared to fresh platelets.

Example 4

Desiccation of Platelet with Fixative Agent (Actual Example)

PRP was processed and prepared as outlined in Example 3. cDHB was prepared as described in Example 1. The overall PRP volume was determined as described in Example 3, and ⅕th that volume of cDHB was added. For example, if the final PRP volume was calculated to be 4 mL, 1 mL of cDHB was added and mixed by inverting the tube several times. The PRP solution was incubated at 34° C. for 1 hour with mixing every 10 minutes.

To fix PRP, glutaraldehyde was added to a final concentration of 0.01% and the PRP was incubated for 1 hour at 34° C. with mixing every 10 minutes. The PRP was then desiccated as described in Example 3.

Vials were sealed under vacuum and/or under nitrogen gas. Samples were packed under vacuum with the appropriate gas as well as having desiccant to control and absorb moisture or gas that may be released by cells under storage. The dried PRP vials were kept at 4° C. or at room temperature.

Depending on the final moisture content, but in general, 0.85 mL of water was used for reconstitution. The recommended volume of distilled water was gently pipetted onto the wall of the vial and was allowed to contact the dried cells via gravity. The time and temperature for reconstitution can range from 5 minutes to 400 minutes at room temperature or temperature up to 37° C. In general, the reconstituted vial was left on a flat surface for 2 hours with gentle swirling every 15 minutes to rehydrate the cells.

Example 5

Desiccation of Non-Adherent Nucleated Cells (Actual Example)

Cells that are naturally non-adherent include B-cells or cells that have been treated with an agent such as EDTA or trypsin that detach them from binding surfaces. Representative cell types include, but are not limited to: stem cells (adult and neonatal, various tissue or species origin), stem cell progenitor cells, gametes (male and female), gamete progenitor cells, endothelial cells, erythroblasts, leukoblasts, chondroblasts, hepatocytes, etc. In the present example, B-cells and stem cells were washed through the process of centrifugation and suspended in fresh media.

The membrane penetrable sugar, such as the non-reducing sugar trehalose (5 to 250 mM), was added to the cell media. Alternatively, a lysosomal membrane stabilizer, such as methylprednisolone sodium succinate=Solu-Medrol (10 µM) is also added to the cell media. Alternatively, a membrane "fluidizer" such as a mild mixture of glycerol (0.1 µm to 20 mM) with a minimal, but effective amount of omega-3 fatty acid (0.1 to 10 µm) is also added to the cell media. Cells were incubated at 37° C. overnight.

The buffer in this example was 0.1 M HEPES with salt components such as 20-60 mM NaCl, 1-5 mM $K_2HPO_4$, adenosine at 70 µM and glucose at 2-5 mM added to the buffer. Also, 5-250 mM trehalose was added to the buffer and also, a membrane impenetrable sugar, such as a neutral dextran 70 (mol. wt. 70 kilodaltons) at 0.1-5% weight by volume was added to the buffer. Alternatively, a fixative agent such as glutaraldehyde at 0.1-0.5% may also be added to the process to stabilize the volume, size and shape of the cells. Cells were incubated for 1 hour at 37° C. prior to desiccation. Cells were washed through the process of centrifugation with media containing 5 to 250 mM trehalose and neutral dextran 70 at 0.1-5% weight by volume. Cells were suspended in buffer at a concentration of 1,000 cells per mL to 100,000,000 cells per mL.

The cells were suspended in a volume of 50 µL to 1000 µL of cDHB, or at any volume and concentration suitable for drying. The cells were transferred to a desiccator with a relative humidity level of 5% or less and heated to 35-45° C. The desiccator was flushed with nitrogen gas and was maintained under nitrogen gas for the duration of the drying process. The dehydration rate was controlled so that the water evaporation was about 0.1-100.0 µL per minute. The dehydration rate can be faster or slower depending on the cell type. The process of drying was considered complete when the relative levels of moisture in the dried cells was suitable for cells to function upon reconstitution. The residual moisture in cells can be 5% to 95%. Dried cells are those at moisture level of 5% to 20%, whereas semi-dried cells are those at moisture level of >20%.

Cells were sealed under vacuum and possibly under nitrogen gas. Samples were packaged under vacuum with appropriate gas as well as having desiccant to control and absorb moisture and/or gas that may be released by cells under storage. The dried cells were kept at 4° C. or at room temperature.

Figure 5:
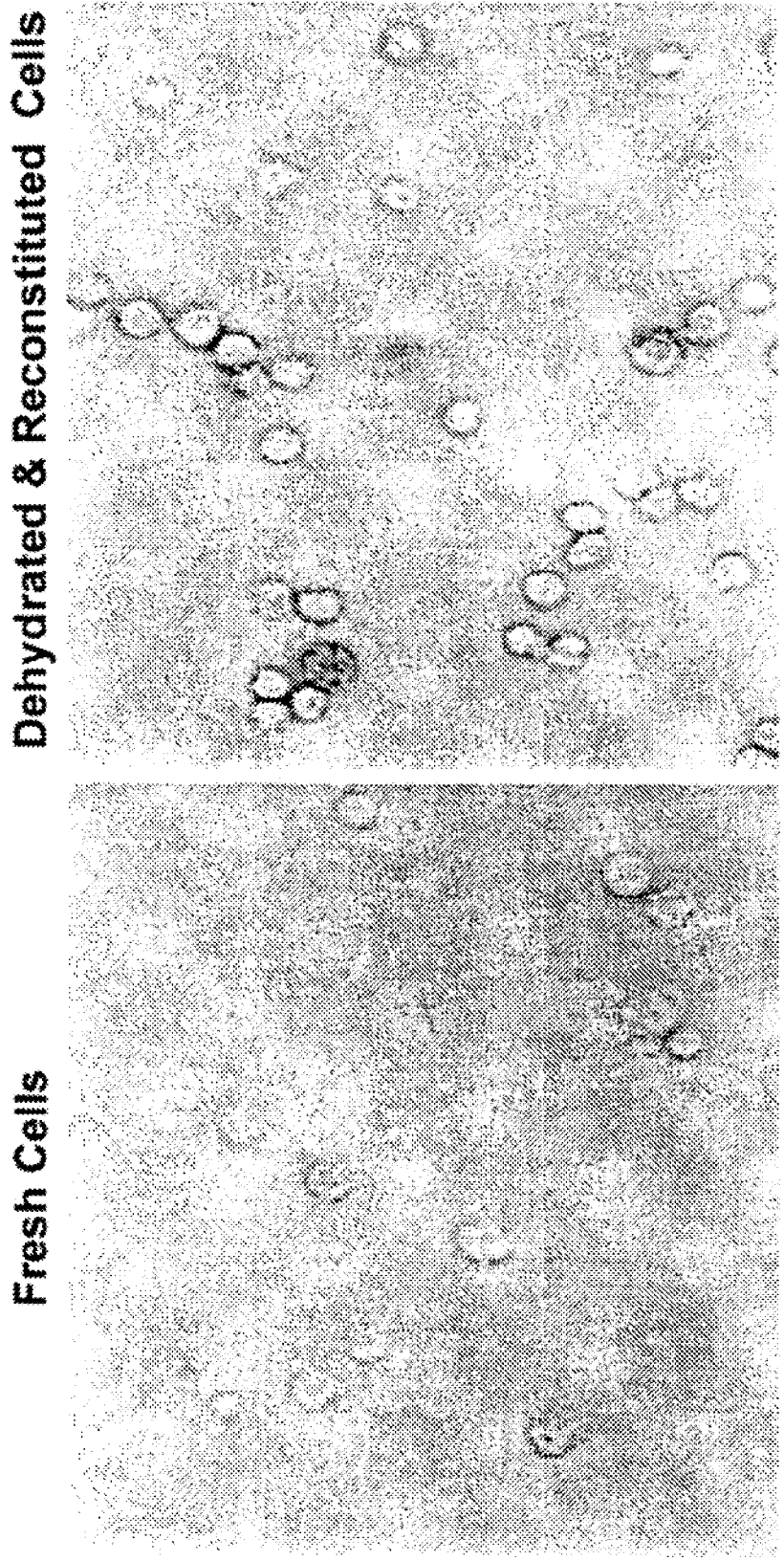
FIG. 5 shows nucleated cells maintain cell membrane integrity upon reconstitution as stained with trypan blue.

Depending on the final moisture content, but in general, 0.75 mL of water was used for reconstitution. The recommended volume of distilled water was gently pipetted onto the wall of the vial and was allowed to contact the dried cells via gravity. The time and temperature for reconstitution can be from about from 5 minutes to about 200 minutes at room temperature or at a temperature up to 37° C. The optimal reconstitution time and temperature will be dependent in the cell type and final use. In general, the reconstituted vial was left on a flat surface for 2 hours with gentle swirling every 15 minutes to rehydrate the cells. FIG. 5 depicts microscopic images of fresh cells and reconstituted cells. As can be seen, the size distribution of the desiccated cells using the current process was similar to that of fresh cells. Furthermore, cells were alive as indicated by the lack of blue dye uptake.

Example 6

Desiccation of Adherent Nucleated Cells (Actual Example)

Representative cell types include: stem cells (adult and neonatal, various tissue or species origin), stem cell progenitor cells, gamete progenitor cells, endothelial cells, erythroblasts, leukoblasts, chondroblasts, hepatocytes, etc. In the present example, endothelial cells were grown in appropriate containers that allowed cells to attach and proliferate to an appropriate density. Then, 5-250 mM trehalose was added to the cell media and cells were incubated at 37° C. overnight.

Media was aspirated from the attached cells and a desiccation buffer (such as, for example, 0.1 M HEPES with salt components such as 20-60 mM NaCl, 1-5 mM $K_2HPO_4$, adenosine at 70 µM and glucose at 2-5 mM) was added. Also, 5-250 mM trehalose was added to the buffer and neutral dextran 70 at 0.1-5% weight by volume was added to the buffer. Alternately, a fixative agent such as glutaraldehyde at 0.1-0.5% can be added to the process to stabilize the volume, size and shape of the cells. Cells were incubated for 1 hour at 37° C. prior to desiccation.

The buffer was aspirated and cell media was added containing 5-250 mM trehalose and neutral dextran 70 at 0.1-5% by weight. The cells were transferred to a desiccator with a relative humidity level of 5% or less and heated to 35-45° C. The desiccator was flushed with nitrogen gas and was maintained under nitrogen gas for the duration of the drying process. The dehydration rate was controlled so that the water evaporation was about 0.1-100.0 µL per minute. The dehydration rate can be faster or slower depending on the cell type. The process of drying was considered complete when the relative level of moisture in the dried cells was suitable for the cells to function upon reconstitution. The residual moisture in the cells can be about 5% to about 95%. Dried cells are those at moisture levels of 5-20%, whereas semi-dried cells are those at moisture levels of >20%-95%.

Cells were sealed under vacuum and/or under nitrogen gas. Samples were packaged under vacuum with the appropriate gas as well as having desiccant to control and absorb moisture or gas that may be released by cells under storage. The dried cells were kept at 4° C. or at room temperature.

Depending on the final moisture content, but in general, 0.75 mL of water was used for reconstitution. The recommended volume of distilled water was gently pipetted onto the wall of the container and allowed to contact the dried cells via gravity. The time and temperature for reconstitution can be from about 5 minutes to about 200 minutes at room temperature or at a temperature up to 37° C. The optimal reconstitution time and temperature will be dependent of cell type and the final use. In general, the reconstituted cells were left on a flat surface for 2 hours with gentle swirling every 15 minutes to rehydrate the cells.

Example 7

Desiccation of Proteins, Nucleic Acids and Viruses (Macromolecules) (Actual Example)

In the present example, various plasma proteins, virus, and conjugated proteins have been studied. Desiccation of macromolecules was conducted by adding trehalose (5-250 mM) and neutral dextran-70 (1%-6% w/v) into the buffer defined for the macromolecules by the end user. The buffer used is determined by the end user and can be any desired buffer such as saline or PBS. For desiccation of macromolecules, the weight of the empty container (tare weight) was determined. In general, a vial made from any material that is non-reactive to cells and proteins was used for this purpose. To desiccate 1 mL of macromolecule solution, a vial with 10 mL capacity was used. For example, a 1 mL aliquot of macromolecule solution was placed into the vial and the vial was weighed again (pre-dehydration weight). The temperature of the dehydration chamber was adjusted to 32° C.-37° C. and dehydrated under vacuum at −560 mmHg open system for 90 minutes or more. The final moisture content was about 5%-15%.

Vials were capped and sealed under vacuum and nitrogen atmosphere. Vials were stored at 4° C. or ambient temperature.

The recommended volume of distilled water was gently pipetted onto the wall of the vial and allowed to contact the dried sample by gravity. In general, 0.85-0.05 mL of water was used for reconstitution. The reconstituted vial was left at 34° C. for 30 minutes with frequent mixing.

Example 8

Desiccation of Whole Blood With and Without Fixative Agent (Actual Example)

The volume of whole blood was determined, and ⅕th the calculated final volume was added as cDHB. To make cDHB, a saline solution (0.9% NaCl) containing 100 mM HEPES was used. To this solution was added 100 mM. Glucose, 10 mM. $K_2HPO_4$, 10% w/v Dextran-70, and 12% w/v Trehalose.

The whole blood solution was incubated at 34° C. for 1 hour with mixing every 10 minutes. Alternatively, to fix whole blood, glutaraldehyde can be added to a final concentration of 0.1% and the whole blood incubated for 1 hour at 34° C. with mixing every 10 minutes. For desiccation of whole blood, the weight of the empty container (tare weight) was determined. In general, a vial made from any material that is non-reactive to cells and proteins was used for this purpose. To desiccate 1 mL of whole blood solution, a vial with 10 mL capacity was used. For example, a 1 mL aliquot of whole blood solution was placed into the vial and the weight of the vial was determined again (pre-dehydration weight). The temperature of the dehydration chamber was adjusted to 32° C.-37° C. and dehydrated under vacuum at −560 mmHg open system for 90 minutes. The final moisture content was about 25%.

Various modifications of the invention, in addition to those described herein, will be apparent to those skilled in the art from the foregoing description. Such modifications are also intended to fall within the scope of the appended claims.

What is claimed is:

1. A method of preserving a cell from a cell line comprising:
   contacting the cell with at least one membrane penetrable sugar;
   contacting the cell with a neutral dextran with a molecular weight greater than or equal to 50,000 daltons;
   optionally, contacting the cell with a fixative agent; and
   drying the cell by vacuum desiccation to a final moisture content of from about 5% to about 90%, wherein the % viability of the dried cell upon rehydration is about 30% or greater.

2. The method of claim 1 wherein the membrane penetrable sugar is trehalose.

3. The method of claim 1 wherein the moisture content is from about 15% to about 40%.

4. The method of claim 1 wherein the moisture content is from about 20% to about 25%.

5. The method of claim 1 wherein the fixative agent is glutaraldehyde or paraformaldehyde.

6. The method of claim 1 wherein the cell is dried by vacuum desiccation at temperatures ranging from about 0° C. to about 40° C. for about 1 hours to about 4 hours.

7. The method of claim 6 wherein the cell is dried by vacuum desiccation at temperatures ranging from about 32° C. to about 34° C. for about 3 hours.

8. The method of claim 7 further comprising storing the cell in a vacuum sealed container in the presence or absence of a desiccant.

9. The method of claim 7 further comprising rehydrating the cell.

10. The method of claim 9 wherein the rehydration comprises contacting the cell with water, optionally followed by saline.

11. The method of claim 9 wherein the rehydration comprises contacting the cell with a physiological buffer.

12. The method of claim 11 wherein the physiological buffer is HEPES, phosphate buffered saline, or a Tris buffer.

13. The method of claim 1 wherein the membrane penetrable sugar is trehalose, the membrane impenetrable sugar is dextran, and the moisture content is from about 15% to about 40%.

14. The method of claim 1 wherein the cell line is Chinese hamster ovary cells, 3T3 fibroblasts, or HEK cells.

15. A method of preserving a cell from a cell line comprising:
   introducing into the cell at least one membrane penetrable sugar by a method consisting of suspending the cell in a solution comprising the at least one membrane penetrable sugar;
   contacting the cell with a neutral dextran with a molecular weight greater than or equal to 50,000 daltons;
   optionally, contacting the cell with a fixative agent; and
   drying the cell by vacuum desiccation to a final moisture content of from about 5% to about 90%.

16. The method of claim 1 wherein the % viability of the dried cell upon rehydration is about 75% or greater.

* * * * *